United States Patent [19]

Heider et al.

[11] 4,154,837

[45] May 15, 1979

[54] (AMINOALKOXY-ARYL)-SUBSTITUTED ISOQUINOLINONES AND NAPHTHYDRINONES AND SALTS THEREOF, AND HYPOTENSIVE COMPOSITIONS AND METHODS EMPLOYING THEM

[75] Inventors: Joachim Heider, Warthausen; Volkhard Austel, Biberach an der Riss; Wolfgang Eberlein, Biberach an der Riss; Rudolf Kadatz, Biberach an der Riss; Jürgen Dämmgen, Warthausen, all of Fed. Rep. of Germany; Walter Kobinger; Christian Lillie, both of Vienna, Austria

[73] Assignee: Boehringer Ingelheim GmbH, Ingelheim am Rhein, Fed. Rep. of Germany

[21] Appl. No.: 867,308

[22] Filed: Jan. 6, 1978

[30] Foreign Application Priority Data

Jan. 22, 1977 [DE] Fed. Rep. of Germany ....... 2702600

[51] Int. Cl.[2] .................................................. A61K 31/47
[52] U.S. Cl. .................................. 424/258; 424/256; 546/141
[58] Field of Search .......... 260/288 D, 295 N, 296 N, 260/287 D, 287 K; 424/256, 258

[56] References Cited

U.S. PATENT DOCUMENTS

| 2,538,341 | 1/1951 | Ullyot ........................ 260/288 D X |
| 3,432,027 | 6/1969 | Sulkowski et al. ......... 260/288 D X |
| 3,993,656 | 11/1976 | Rooney et al. ................. 260/296 N |
| 4,067,873 | 1/1978 | Troxler et al. .................. 260/288 D |

*Primary Examiner*—Donald G. Daus
*Assistant Examiner*—Diana G. Rivers
*Attorney, Agent, or Firm*—Hammond & Littell

[57] ABSTRACT

Compounds of the formula

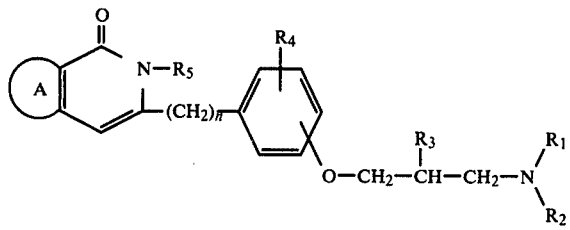

wherein

A is benzo, mono-, di- or tri-substituted benzo, the substituents being selected from the group consisting of lower alkoxy, amino and nitro, or pyrido;

$R_1$ is hydrogen or lower alkyl;

$R_2$ is alkyl of 1 to 6 carbon atoms or $-X-R_6$, where X is straight alkylene of 1 to 4 carbon atoms or hydroxy-substituted straight alkylene of 1 to 4 carbon atoms; and $R_6$ is amino; carbalkoxy of 2 to 6 carbon atoms; phenyl; mono-, di- or tri-substituted phenyl, the substituents being selected from the group consisting of lower alkyl and lower alkoxy; phenoxy; or mono-, di- or tri-substituted phenoxy, the substituents being selected from the group consisting of lower alkyl and lower alkoxy;

$R_3$ is hydrogen or hydroxyl;

$R_4$ is hydrogen, lower alkyl or lower alkoxy;

$R_5$ is hydrogen or lower alkyl; and n is 0, 1 or 2;

and non-toxic, pharmacologically acceptable acid addition salts thereof. The compounds as well as the salts are useful as antiarrhythmics, β-adrenergic-receptor blockers and anti-anginous agents.

9 Claims, No Drawings

(AMINOALKOXY-ARYL)-SUBSTITUTED ISOQUINOLINONES AND NAPHTHYDRINONES AND SALTS THEREOF, AND HYPOTENSIVE COMPOSITIONS AND METHODS EMPLOYING THEM

This invention relates to novel 3-substituted isoquinolin-1(2H)-ones and 1,6-, 2,6-, 3,6- or 4,6-naphthydrin-5(6H)-ones and non-toxic acid addition salts thereof, as well as to methods of preparing these compounds.

More particularly, the present invention relates to a novel class of compounds represented by the formula (I)

wherein
- A is benzo, mono-, di- or tri-substituted benzo, the substituents being selected from the group consisting of lower alkoxy, amino and nitro, or pyrido;
- $R_1$ is hydrogen or lower alkyl;
- $R_2$ is alkyl of 1 to 6 carbon atoms or $-X-R_6$, where X is straight alkylene of 1 to 4 carbon atoms or hydroxy-substituted straight alkylene of 1 to 4 carbon atoms; and
  - $R_6$ is amino; carbalkoxy of 2 to 6 carbon atoms; phenyl; mono-, di- or tri-substituted phenyl, the substituents being selected from the group consisting of lower alkyl and lower alkoxy; phenoxy; or mono-, di- or tri-substituted phenoxy, the substituents being selected from the group consisting of lower alkyl and lower alkoxy;
- $R_3$ is hydrogen or hydroxyl;
- $R_4$ is hydrogen, lower alkyl or lower alkoxy;
- $R_5$ is hydrogen or lower alkyl; and
- n is 0, 1 or 2;

and non-toxic, pharmacologically acceptable acid addition salts thereof.

The term "lower alkyl" is intended to include primarily alkyl of 1 to 3 carbon atoms, such as methyl, ethyl, propyl or isopropyl. Similarly, "lower alkoxy" is intended to mean primarily alkoxy of 1 to 3 carbon atoms, such as methoxy, ethoxy, propoxy or isopropoxy.

Examples of specific and preferred embodiments of variants A, $R_1$, $R_2$, $R_4$, $R_5$ and $R_6$ in formula I are the following:

- A—Benzo, methoxy-benzo, dimethoxy-benzo and pyrido;
- $R_1$—Hydrogen, methyl, ethyl, propyl and isopropyl;
- $R_2$—Methyl, ethyl, n-propyl, n-butyl, n-pentyl, n-hexyl, isopropyl, isobutyl, isoamyl, tert. butyl and tert. pentyl;
- X—Methylene, ethylene, hydroxyethylene, propylene, hydroxypropylene and butylene;
- $R_6$—Phenyl, methoxyphenyl, dimethoxyphenyl, trimethyoxyphenyl, methylphenyl, amino, carbomethoxy, carbethoxy, carbopropoxy, carbobutoxy, carbopentoxy, carbisopropoxy, carbo-tert. butoxy, carbo-tert. pentoxy, phenoxy, methylphenoxy and methoxyphenoxy;
- $R_4$—Hydrogen, methoxy, ethoxy, propoxy and isopropoxy;
- $R_5$—Methyl, ethyl, propyl and isopropyl.

A preferred sub-genus under the genus defined by formula I is consistituted by compounds of that formula wherein
- A is benzo, methoxybenzo, dimethoxybenzo or pyrido;
- $R_1$ is hydrogen, methyl or ethyl;
- $R_2$ is ethyl, isopropyl or tert. butyl;
- X is straight alkylene of 2 to 3 carbon atoms or hydroxy-substituted straight alkylene of 2 to 3 carbon atoms;
- $R_6$ is phenyl; methoxyphenyl, especially 2-methoxyphenyl or 4-methoxy-phenyl; dimethoxyphenyl, especially 3,4-dimethoxy-phenyl; trimethoxyphenyl, especially 3,4,5-trimethoxy-phenyl; amino; tolyl; isopropoxycarbonyl; tert. butoxycarbonyl; phenoxy; methylphenoxy, especially 2-methyl-phenyl or 4-methyl-phenyl; or methoxyphenoxy, especially 2-methoxy-phenoxy or 4-methoxy-phenoxy;
- $R_3$ is hydrogen or hydroxyl;
- $R_4$ is hydrogen or methoxy;
- $R_5$ is methyl; and
- n is 0, 1 or 2;

and non-toxic, pharmacologically acceptable acid addition salts thereof.

A further, especially preferred sub-genus is constituted by compounds of the formula I wherein A is benzo, 2-methoxy-benzo or 2,3-dimethoxy-benzo;
- $R_1$ is hydrogen;
- $R_2$ is isopropyl or tert. butyl;
- $R_3$ is hydroxyl;
- $R_4$ is hydrogen or methoxy;
- $R_5$ is methyl; and
- n is 0, 1 or 2;

and non-toxic, pharmacologically acceptable acid addition salts thereof.

The compounds embraced by formula I may be prepared by the following methods:

Method A

By reacting a compounds of the formula (II)

wherein
A, $R_3$, $R_4$, $R_5$ and n have the same meanings as in formula I, and
Y is a nucleophilic exchangeable substituent such as halogen or, together with $R_3$, oxygen,
with an amine of the formula wherein $R_1$ and $R_2$ have the same meanings as in formula I.

The reaction is optionally carried out in the presence of an inert organic solvent, such as isopropanol, tetrahydrofuran, dimethylformanide or dimethylsulfoxide, and optionally in the presence of an acid-binding agent, such as an alkali metal alcoholate or an alkali metal carbonate, and, if required, in a closed pressure vessel at a temperature between 50° and 200° C., preferably between 80° and 160° C. Of particular advantage is the use of a sufficient excess of the amine of the formula III as the solvent medium for the reaction.

Method B

By reacting a carboxylic acid of the formula

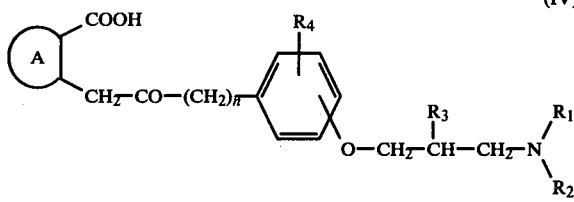

where A, $R_1$, $R_2$, $R_3$, $R_4$ and n have the same meanings as in
formula I,
or a reactive derivative thereof, with an amine of the formula $R_5$—$NH_2$                (V)

wherein $R_5$ has the same meanings as in formula I.

The reaction is optionally carried out in an inert organic solvent, such as methanol, ethanol, isopropanol, dioxane or dimethylformanide, and optionally in the presence of an condensation agent such as an alkali metal alcoholate, and, if required, in a closed pressure vessel at a temperature between 50° and 200° C., preferably between 80° and 140° C. Of particular advantage is the use of a sufficient excess of the amine of the formula V as the solvent medium.

The compounds of the formula I are organic bases and therefore form acid addition salts with inorganic or organic acids. Examples of non-toxic, pharmacologically acceptable acid addition salts are those formed with hydrochloric acid, hydrobromic acid, sulfuric acid, phosphoric acid, lactic acid, citric acid, tartaric acid, oxalic acid, maleic acid, 8-chlorotheophylline or the like.

The starting compounds of the formulas II, III, IV and V are either described in the literature or an be prepared by processes disclosed in the literature.

For instance, a compound of the formula II is obtained by reacting a corresponding o-halo-carboxylic acid of the formula

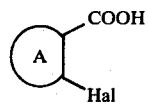

where
A has the same meanings as in formula I, and
Hal is chlorine, bromine or iodine,
with a ketone of the formula

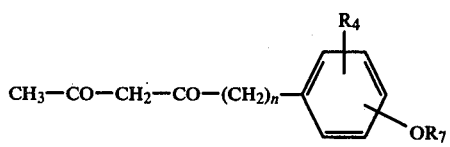

wherein
$R_4$ and n have the same meanings as in formula I, and
$R_7$ is methyl or benzyl,
advantageously in the presence of copper acetate as a catalyst, and in the presence of a sodium alcoholate, such as sodium ethylate, as an acid acceptor, at a temperature between 60° and 100° C.

The intermediate carboxylic acid thus obtained of the formula

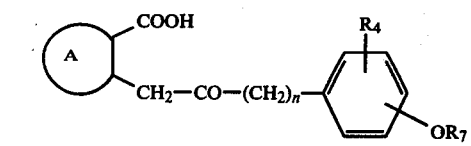

wherein A, $R_4$, $R_7$ and n have the meanings previously defined, is subsequently reacted with an amine of the formula V to form the cyclic ketone of the formula

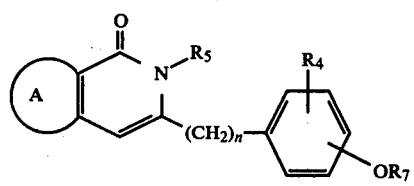

wherein A, $R_4$, $R_5$, $R_7$ and n have the meanings previously defined. After removal of the substituent $R_7$ and reaction of the hydroxy compound with a corresponding halo-epihydrin of with 1-bromo-3-chloro-propane in the presence an inert solvent, such as dimethylformanide or dimethylsulfoxide, in the presence of sodium ethylate at room temperature, the desired compound of the formula II is obtained.

A starting compound of the formula IV is obtained by reacting a compound of the formula

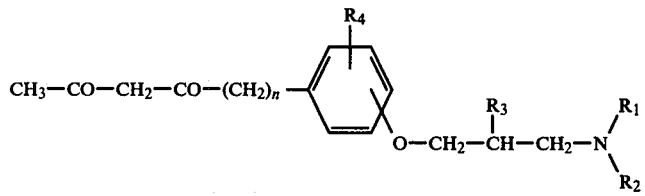

wherein $R_1$, $R_2$, $R_3$, $R_4$ and n have the same meanings as in formula I, with an o-halo-carboxylic acid of the formula VI, preferably in the presence of sodium ethylate and at a temperature between 60° and 100° C.

The following examples illustrate the present invention and will enable others skilled in the art to understand it more completely. It should be understood, however, that the invention is not limited solely to the particular examples given below.

The structure of the novel end products was comfirmed by means of their IV-, UV- and NMR-spectra, as well as by elemental analysis.

EXAMPLE 1

2-Methyl-3-[4-(2-hydroxy-3-tert.butylamino-propoxy)-phenyl]-7-methoxy-isoquinolin-1(2H)-one by method A (a)  2-Methyl-3-[4-(2,3-epoxypropoxy)-phenyl]-7-methoxy-isoquinolin-1(2H)-one 1.35 gm (10 mmols+20%) of potassium-tert.butoxide were added to a solution of 2.8 gm (10 mmols) of 2-methyl-3-(4-hydroxy-phenyl)-7-methoxy-isoquinolin-1(2H)-one in 20 ml of dimethylsulfoxide, while stirring; the potassium salt precipitated out after a short time. 2.8 ml of epibromohydrin were now added, and the mixture was stirred at room temperature until the reaction had gone to completion. The reaction mixture was then poured into ice water, and the cristalline precipitate was collected by suction filtration, washed and dried.

Yield: 2.86 gm (85% of theory) M.p.: 153°–155° C.
$C_{19}H_{20}NO_4$(337.37) Calculated: C-71.20%; H-5.68%; N-4.15% Found: C-71.14%; H-5.65%; N-4.10%

(b) 2.55 gm (7.5 mmols) of the epoxide obtained in step (a) were heated with 25 ml of tert.butylamine at 120° C. in a closed steel vessel. After 2 hours the unreacted excess of the amine was removed in vacuo, and the resulting granular residue was recrystallized from acetone, yielding 2.1 gm (70% of theory) of the compound of the formula

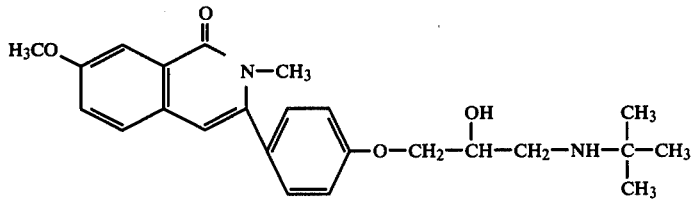

which had a melting point of 130°–131° C.

Elemental analysis: $C_{24}H_{30}N_2O_4$(410.51) Calculated: C-70.22%; H-7.32%; N-6.82% Found: C-69.90%; H-7.29%; N-6.75%

EXAMPLE 2

2-Methyl-3-[4-(2-hydroxy-3-(N-3,4-dimethoxyphenethyl-N-ethyl-amino)-propoxy)-phenyl]-7-methoxy-isoquinolin-1(2H)-one and its oxalate by method A.

1.4 gm (5 mmols) of 2-methyl-3-[4-(2,3-epoxypropoxy)-phenyl]-7-methoxy-isoquinolin-1(2H)-one, obtained according to example (1a), were reacted with 1.5 gm of N-3,4-dimethoxyphenethyl-N-ethylamine at 140° C. After the reaction had gone to completion, the obtained raw product was purified on a silica gel column (grain-size: 0.2–0.5 mm, eluant: chloroform:methanol = 19:1). After evaporation of the elvate, the obtained product was dissovled in acetone and precipitated by means of ethereal oxalic acid to its ovalate, yielding 76.5% of theory of the oxalate of the formula

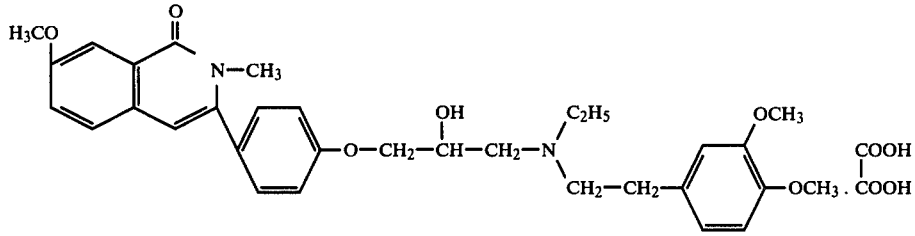

which had a melting point of 152°–155° C. (recrystallized from methanol).

Elemental analysis: $C_{34}H_{40}N_2O_{10}$ (636.70) Calculated: C-64.14%; H-6.33%; N-4.40% Found: C-63.86%; H-6.46%; N-4.36%

EXAMPLE 3

2-Methyl-3-[4-(3-(N-3,4-dimethoxyphenethyl-N-methylamino)-propoxy)-phenyl]-7-methoxy-isoquinolin-1(2H)-one and its hydrochloride by method A.

(a)  2-Methyl-3-[4-(3-chloropropoxy)-phenyl]-7-methoxy-isoquinolin-1(2H)-one 1.35 gm (10 mmols+20%) of potassium-tert. butoxide were added to a stirred solution of 2.8 gm (10 mmols) of 2-methyl-3-(4-hydroxy-phenyl)-7-methoxy-isoquinolin-1 (2H)-one in 20 ml of dimethylsulfoxide; the potassium salt precipitated out after a short time. 2.8 ml of 1-bromo-3-chloropropane were now added to the mixture, and stirring was continued at room temperatures. After the reaction had gone to completion, the reaction mixture was poured into ice water, and the aqueous mixture was extracted with ethyl acetate. The combined organic extracts were dried over sodium sulfate and evaporated in vacuo. The residual colorless oil solidified and was recrystallized from acetone/ether.

Yield: 3.2 gm (89.6% of theory) M.p.: 102°–104° C.

$C_{20}H_{20}ClNO_3$(357.83) Calculated: C-67.13%; H-5.63%; N-3.91%; Cl-9.90% Found: C-66.97%; H-5.61%; N-3.96%; Cl-9.65%

(b) 1.8 gm (5 mmols) of the end product of step (a) were reacted with 1.8 gm of N-3,4-dimethoxyphenylethyl-N-methyl-amine at 140° C. After the reaction had gone to completion, the obtained raw product was purified on a silican gel column (grain size: 0.2–0.5 mm; eluant: chloroform:methanol = 19:1). After evaporation of the eluate, the residual free base was dissolved in acetone, and the hydrochloride was precipitated with ethereal hydrochloric acid.

Yield: 1.45 gm (52.5% of theory) M.p.: 155°–160° C. (from acetone) Elemental analysis: $C_{31}H_{37}ClN_2O_5$ (553.09) Calculated: C-67.32%; H-6.74%; N-5.07%; Cl-6.41% Found: C-67.00%; H-6.84%; N-4.98%; Cl-6.31%

EXAMPLE 4

2-Methyl-3-[4-(2-hydroxy-3-isopropylamino-propoxy)-phenyl]-7-methoxy-isoquinolin-1(2H)-one was prepared analogous to Example (1b) from 2-methyl-3-[4-(2,3-epoxypropoxy)-phenyl]-7-methoxy-isoquinolin-1(2H)-one and isopropylamine at a reaction temperature of 50° C.

Yield: 63% of theory M.p.: 140°–142° C. Elemental analysis: $C_{23}H_{28}N_2O_4$ (396.48) Calculated: C-69.68%; H-7.12%; N-7.06% Found: C-69.38%; H-7.14%; N-7.10%

EXAMPLE 5

2-Methyl-3-[4-(2-hydroxy-3-(3,4-dimethoxyphenethyl-amino)-propoxy-phenyl]-7-methoxy-isoquinolin-1(2H)-one oxalate was prepared analogous to Example 2 from 2-methyl-3-[4-(2,3-epoxypropoxy)-phenyl]-7-methoxy-isoquinolin-1(2H)-one and 3,4-dimethoxyphenethylamine.

Yield: 71% of theory M.p.: 208°–210° C. (from acetone) Elemental analysis: $C_{32}H_{36}N_2O_{10}$ (608.64) Calculated: C-63.14%: H-5.96%; N-4.59% Found: C-62.68%; H-5.90%; N-4.49%

EXAMPLE 6

2-Methyl-3-[2-(2-hydroxy-3-isopropylamino-propoxy)-phenyl]-7-methoxy-isoquinolin-1(2H)-one oxalate was prepared analogous to Example 1b from 2-methyl-3-[2-(2,3-epoxypropoxy)-phenyl]-7-methoxy-isoquinolin-1(2H)-one and isopropylamine.

Yield: 82.8% of theory M.p.: 216°–218° C. (from methanol) Elemental analysis: $C_{25}H_{30}N_2O_8$ (486.50) Calculated: C-61.72%; H-6.22%; N-5.76% Found: C-61.70%; H-6.33%; N-6.18%

EXAMPLE 7

2-Methyl-3-[2-(2-hydroxy-3-isopropylamino-propoxy)-4-methoxy-phenyl]-7-methoxy-isoquinolin-1(2H)-one oxalate was prepared analogous to Example 1b from 2-methyl-3-[2-(2,3-epoxypropoxy)-4-methoxy-phenyl]-7-methoxy-isoquinoline-1(2H)-one and isopropylamine.

Yield: 88% of theory M.p.: 165°–168° C. (from methanol) Elemental analysis: $C_{26}H_{32}N_2O_9$ (516.55) Calculated: C-60.45%; H-6.24%; N-5.42% Found: C-61.28%; H-6.16%; N-5.38%

EXAMPLE 8

2-Methyl-3-[2-hydroxy-3-tert. butylamino-propoxy)-4-methoxy-phenyl]-7-methoxy-isoquinolin-1(2H)-one oxalate was prepared analogous to Example 1b from 2-methyl-3-[2-(2,3-epoxypropoxy)-4-methoxy-phenyl]-7-methoxy-isoquinoline-1(2H)-one and tert. butylamine.

Yield: 90% of theory M.p.: 115°–120° C. (from acetone/ether) Elemental analysis: $C_{27}H_{34}N_2O_9$ (530.55) Calculated: C-61.12%; H-6.46%; N-5.28% Found: C-60.91%; H-6.32%; N-5.19%

EXAMPLE 9

2-Methyl-3-[4-(2-hydroxy-3-tert. butylamino-propoxy)-phenyl]-6,7-dimethoxy-isoquinolin-1(2H)-one was prepared analogous to Example 1b from 2-methyl-3-[4-(2,3-epoxypropoxy-phenyl]-6,7-dimethoxy-isoquinolin-1(2H)-one and tert. butylamine.

Yield: 65% of theory M.p.: 165°–166° C. (from acetone/ether) Elemental analysis: $C_{25}H_{32}N_2O_5$ (440.53) Calculated: C-68.15%; H-7.32%; N-6.36% Found: C-67.70; H-7.23; N-6.41%

EXAMPLE 10

2-Methyl-3-[4-(2-hydroxy-3-isopropylamino-propoxy)-phenyl]-6,7-dimethoxy-isoquinoline-1(2H)-one was prepared analogous to Example 1b from 2-methyl-3-[4-(2,3-epoxypropoxy)-phenyl]-6,7-dimethoxy-isoquinolin-1(2H)-one and isopropylamine.

Yield: 81% of theory M.p.: 206°–207° C. (from acetone/ether) Elemental analysis: $C_{24}H_{30}N_2O_5$ (426.50) Calculated: C-67.58%; H-7.09%; N-6.57% Found: C-67.36%; H-7.02%; N-6.63%

EXAMPLE 11

2-Methyl-3-[3-methoxy-4-(2-hydroxy-3-isopropylamino-propoxy)-phenyl]-7-methoxy-isoquinolin-1(2H)-one was prepared analogous to Example 1b from 2-methyl-3-[3-methoxy-4-(2,3-epoxypropoxy)-phenyl]-7-methoxy-isoquinolin-1(2H)-one and isopropylamine.

Yield: 77% of theory M.p.: 144°–146° C. (from acetone) Elemental analysis: $C_{24}H_{30}N_2O_5$ (426.50) Calculated: C-67.58; H-7.09%; N-6.57% Found: C-67.35%; H-7.15%; N-6.76%

EXAMPLE 12

2-Methyl-3-[3-methoxy-4-(2-hydroxy-3-(2-methoxyphenylethyl-amino)-propoxy)-phenyl]-7-methoxy-isoquinolin-1(2H)-one oxalate was prepared analogous to Example 2 from 2-methyl-3-[3-methoxy-4-(2,3-epoxypropoxy)-phenyl]-7-methoxy-isoquinolin-1(2H)-one and 2-methoxyphenethyl-amine.

Yield: 56% of theory M.p.: 197°–199° C. (from methanol) Elemental analysis: $C_{32}H_{36}N_2O_{10}$ (608.65) Calculated: C-63.18%; H-6.04; N-4.60% Found: C-63.40%; H-6.11%; N-4.56%

EXAMPLE 13

2-Methyl-3-[4-(2-hydroxy-3-isopropylamino-propoxy)-phenethyl]-7-methoxy-isoquinolin-1(2H)-one was prepared analogous to Example 1b from 2-methyl-3-[4-(2,3-epoxypropoxy)-phenethyl]-7-methoxy-isoquinolin-1(2H)-one and isopropylamine.

Yield: 77% of theory M.p.: 137°–139° C. (from acetone/ether) Elemental analysis: $C_{25}H_{32}N_2O_4$ (424,5) Calculated: C-70.75%; H-7.59%; N-6.60% Found: C-70.40%; H-7.48%; N-6.61%

EXAMPLE 14

2-Methyl-3-[3-methoxy-4-(2-hydroxy-3-isopropylamino-propoxy)-phenethyl]-7-methoxy-isoquinolin-1(2H)-one was prepared analogous to Example 1b from 2-methyl-3-[3-methoxy-4-(2,3-epoxypropoxy)-phenethyl]-7-methoxy-isoquinolin-1(2H)-one and isopropylamine.

Yield: 80% of theory M.p.: 162°–164° C. (from acetone/ether) Elemental analysis: $C_{26}H_{34}N_2O_5$ (454.56) Calculated: C-68.70%; H-7.54%; N-6.16% Found: C-68.60%; H-7.54%; N-6.03%

EXAMPLE 15

2-Methyl-3-[3-methoxy-4-(3-(2-o-methoxy-phenylethyl-amino)-2-hydroxy)-propoxy)-phenethyl]-7-methoxy-isoquinolin-1(2H)-one was prepared analogous to Example 2 from 2-methyl-3-[3-methoxy-4-(2,3-epoxypropoxy)-phenethyl]-7-methoxy-isoquinolin-1(2H)-one and 2-methoxyphenyl-ethylamine.

Yield: 74% of theory M.p.: 117°–118° C. (from acetone) Elemental analysis: $C_{32}H_{38}N_2O_6$ (546.67) Calculated: C-70.30%; H-7.01%; N-5.13% Found: C-70.20%; H-7.03%; N-5.04%

EXAMPLE 16

2-Methyl-3-[4-(2-hydroxy-3-tert. butylamino-propoxy)-phenyl]-isoquinolin-1(2H)-one was prepared analogous to Example 1b from 2-methyl-3-[4-(2,3-epoxypropoxy)-phenyl]-isoquinolin-1(2H)-one and tert. butylamine.

Yield: 84% of theory M.p.: 130°–132° C. (from acetone/ether) Elemental analysis: $C_{23}H_{28}N_2O_3$ (380.48) Calculated: C-72.61%; H-7.42; N-7.36% Found: C-72.80%; H-7.48; N-7.22%

EXAMPLE 17

2-Methyl-3-[4-(3-(N-4-methoxyphenethyl-N-methyl-amino)-propoxy)-phenyl]-7-methoxy-isoquinolin-1(2H)-one hydrochloride was prepared analogous to Example 3b from 2-methyl-3-[4-(3-chloropropoxy)-phenyl]-7-methoxy-isoquinoline-1(2H)-one and N-b 4-methoxyphenethyl-N-methyl-amine.

Yield: 75% of theory M.p.: 229°–230° C. (from acetone/ether) Elemental analysis: $C_{30}H_{35}ClN_2O_4$ (523.07) Calculated: C-68.88%; H-6.75%; N-5.36%; Cl-6.78 Found: C-68.60%; H-6.70%; N-5.36%; Cl-6.82

EXAMPLE 18

2-Methyl-3-[4-(3-(N-3,4,5-trimethoxyphenethyl-N-methyl-amino)-propoxy)-phenyl]-7-methoxy-isoquinolin-1(2H)-one oxalate was prepared analogous to Example 3b from 2-methyl-3-[4-3-chloropropoxy)-phenyl]-7-methoxy-isoquinolin-1(2H)-one and N-3,4,5-trimethoxyphenethyl-N-methyl-amine.

Yield: 53% of theory (as oxalate) M.p.: 224°–225° C. (from methanol) Elemental analysis: $C_{34}H_{40}N_2O_{10}$ (636.68) Calculated: C-64.13% H-6.33% N-4.40% Found: C-63.71%; C-6.19%; C-4.55%

EXAMPLE 19

2-Methyl-3-[4-(3-(2-hydroxy-3-o-cresyl-propylamino)-propoxy)-phenyl]-7-methoxy-isoquinolin-1(2H)-one oxalate was prepared analogous to Example 3b from 2-methyl-3-[4-(3-chloropropoxy)-phenyl]7-methoxy-isoquinolin-1(2H)-one and 2-hydroxy-3-o-cresyl-propylamine.

Yield: 70% of theory M.p.: 178°–182° C. (from methanol) Elemental analysis: $C_{32}H_{36}N_2O_9$ (592.65) Calculated: C-64.85%; H-6.12%; N-4.73% Found: C-64.50%; H-6.21%; N-4.66%

EXAMPLE 20

2-Methyl-3-[4-(3-(2-hydroxy-3-p-cresyl-propylamine)-propoxy)-phenyl]-7-methoxy-isoquinolin-1(2H)-one oxalate was prepared analogous to Example 3b from 2-methyl-3-[4-(3-chloropropoxy)-phenyl]-7-methoxy-isoquinolin-1(2H)-one and 2-hydroxy-3-p-cresyl-propylamine.

Yield: 64% of theory M.p.: 195°–197° C. (from methanol) Elemental analysis: $C_{32}H_{36}N_2O_9$ (592.65) Calculated: C-64.85%; H-6.12%; N-4.73% Found: C-64.70%; H-6.13%; N-4.83%

EXAMPLE 21

2-Methyl-3-[4-(3-(2-hydroxy-3-o-methoxyphenoxy-propyl-amino)-propoxy)-phenyl]-7-methoxy-isoquinolin-1(2H)-one oxalate was prepared analogous to example 3b from 2-methyl-3-[4-(3-chloropropoxy)-phenyl]-7-methoxy-isoquinolin-1(2H)-one and 2-hydroxy-3-o-methoxy-phenoxy-propylamine.

Yield: 77% of theory M.p.: 156°–158° C. (from methanol) Elemental analysis: $C_{32}H_{36}N_2O_{10}$ (608.65) Calculated: C-63.14%; H-5.96%; N-4.60% Found: C-62.78%; H-5.74%; N-4.59%

EXAMPLE 22

2-Methyl-3-[4-(3-(2-hydroxy-3-p-methoxyphenoxy-propyl-amino)-propoxy)-phenyl]-7-methoxy-isoquinolin-1(2H)-one oxalate was prepared analogous to Example 3b from 2-methyl-3-[4-(3-chloropropoxy)-phenyl]-7-methoxy-isoquinolin-1(2H)-one and 2-hydroxy-3-p-methoxy-phenoxy-propylamine.

Yield: 77% of theory (as oxalate) M.p.: 172°–175° C. (from methanol) Elemental analysis: $C_{32}H_{36}N_2O_{10}$ (608.65) Calculated: C-63.14; H-5.96%; N-4.60% Found: C-62.92%; H-5.91%; N-4.46%

EXAMPLE 23

2-Methyl-3-[4-(3-(2-methoxyphenethyl-amino)-propoxy)-phenyl]-7-methoxy-isoquinolin-1(2H)-one oxalate was prepared analogous to Example 3b from 2-methyl-3-[4-(3-chloropropoxy)-phenyl]-7-methoxy-isoquinolin-1(2H)-one and 2-methoxyphenethyl-amine.

Yield: 67% of theory M.p.: 216°–218° C. (from methanol) Elemental analysis: $C_{31}H_{34}N_2O_8$ (562.60) Calculated: C-66.18%; H-6.09%; N-4.98% Found: C-66.10%; H-6.18%; N-4.85%

EXAMPLE 24

2-Methyl-3-[4-(3-(3-aminopropyl-amino)-propoxy)-phenyl]-7-methoxy-isoquinolin-1(2H)-one dioxalate was prepared analogous to Example 3b from 2-methyl-3-[4-(3-chloropropoxy)-phenyl]-7-methoxy-isoquinolin-1(2H)-one and 1,3-diamino-propane.

Yield: 50.8% of theory M.p.: 220°–225° C. (from methanol) Elemental analysis: $C_{27}H_{33}N_3O_{11}$ (575.56) Calculated: C-58.50%; H-5.95%; N-6.45% Found: C-58.33%; H-5.87%; N-6.30%

EXAMPLE 25

2-Methyl-3-[4-(3-(2-hydroxy-3-phenoxy-propylamino)-propoxy)-phenyl]-7-methoxy-isoquinolin-1(2H)-one oxalate was prepared analogous to Example 3b from 2-methyl-3-[4-(3-chloropropoxy)-phenyl]-7-methoxy-isoquinolin-1(2H)-one and 2-hydroxy-3-phenoxy-propylamine.

Yield: 73% of theory M.p.: 170°–175° C. (from methanol) Elemental analysis: $C_{31}H_{34}N_2O_9$ (578.60) Calculated: C-64.35%; H-5.92%; N-4.84% Found: C-63.70%; H-5.96%; N-4.89%

EXAMPLE 26

2-Methyl-3-[4-(3-(2-hydroxy-2-phenyl-ethyl-amino)-propoxy)-phenyl]-7-methoxy-isoquinolin-1(2H)-one oxalate was prepared analogous to Example 3b from 2-methyl-3-[4-(3-chloropropoxy)-phenyl]-7-methoxy-isoquinolin-1(2H)-one and 2-hydroxy-2-phenyl-ethyl-amine.

Yield: 74% of theory M.p.: 215°–220° C. (from methanol) Elemental analysis: $C_{30}H_{32}N_2O_8$ (458.55) Calculated: C-65.68%; H-5.88%; N-5.11% Found: C-65.83%; H-5.88%; N-5.26%

EXAMPLE 27

2-Methyl-3-[4-(3-(2-amino-ethyl-amino)-propoxy)-phenyl]-7-methoxy-isoquinolin-1(2H)-one dioxalate was prepared analogous to Example 3b from 2-methyl-3-[4-(3-chloropropoxy)-phenyl]-7-methoxy-isoquinolin-1(2H)-one and 1.2-diamino-ethane.

Yield: 73% of theory M.p.: 235°–240° C. (from methanol) Elemental analysis: $C_{26}H_{31}N_3O_{11}$ (561.56) Calculated: C-55.61%; H-5.56%; N-7.46% Found: C-55.87%; H-5.64%; N-7.38%

EXAMPLE 28

2-Methyl-3-[4-(3-(3-m-toluidine-propyl-amino)-propoxy)-phenyl]-7-methoxy-isoquinolin-1(2H)-one hydrochloride was prepared analogous to Example 3b from 2-methyl-3-[4-(3-chloropropoxy)-phenyl]-7-methoxy-isoquinolino-1(2H)-one and 3-m-toluidine-propyl-amine.

Yield: 50% of theory M.p.: 204°–205° C. (from acetone) Elemental analysis: $C_{30}H_{36}ClN_3O_3$ (522.16) Calculated: C-69.00%; H-6.95%; N-8.05%; Cl-6.79% Found: C-68.90%; H-7.12%; N-8.03%; Cl-6.80%

EXAMPLE 29

2-Methyl-3-[4-(3-(2-isopropoxycarbonyl-ethyl-amino)-propoxy)-phenyl]-7-methoxy-isoquinolin-1(2H)-one oxalate was prepared analogous to Example 3b from 2-methyl-3-[4-(3-chloropropoxy)-phenyl]-7-methoxy-isoquinolin-1(2H)-one and isopropyl β-amino-propionate.

Yield: 53% of theory M.p.: 174°–175° C. (from acetone) Elemental analysis: $C_{28}H_{34}N_2O_9$ (542.58) Calculated: C:61.08%; H-6.32%; N-5.16% Found: C-61.70%; H-6.53%; N-5.23%

EXAMPLE 30

2-Methyl-3-[4-(3-(2-isobutoxycarbonyl-ethyl-amino)-propoxy-phenyl]-7-methoxy-isoquinolin-1(2H)-one oxalate was prepared analogous to Example 3b from 2-methyl-3-[4-(3-chloropropoxy)-phenyl]-7-methoxy-isoquinolin-1(2H)-one and isobutyl β-amino-propionate.

Yield: 22% of theory M.p.: 190°–195° C. (from acetone) Elemental analysis: $C_{29}H_{36}N_2O_9$ (556.62) Calculated: C-62.57%; H-6.52%; N-5.03% Found: C-62.90%; H-6.66%; N-5.03%

EXAMPLE 31

6-Methyl-7-[4-(2-hydroxy-3-(3,4-dimethoxy-phenethyl-N-methyl-amino)-propoxy)-phenyl]-1,6-naphthyridin-5(6H)-one oxalate of the formula

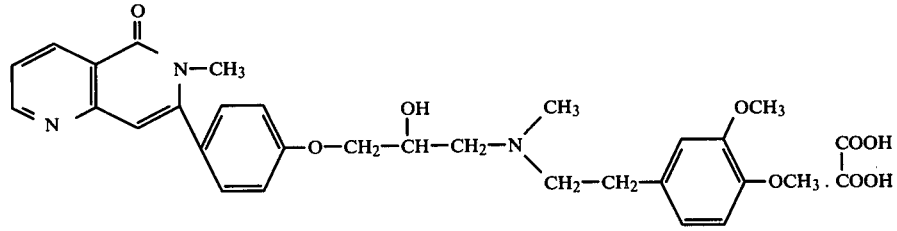

was prepared analogous to Example 2 from 6-methyl-7-[4-(2,3-epoxypropoxy)-phenyl]-1,6-naphthyridin-5(6H)-one and N-[2-(3,4-dimethoxyphenyl)-ethyl]-N-methyl-amine.

Yield: 70% of theory M.p.: 85°–95° C. Elemental analysis: $C_{31}H_{35}N_3O_9$ (593.6) Calculated: C-62.72%; H-5.94%; N-7.08% Found: C-62.22%; H-5.95%; N-6.98%

EXAMPLE 32

6-Methyl-7-[4-(2-hydroxy-3-isopropylamino-propoxy)-phenyl]-1,6-naphthyridin-5(6H)-one was prepared analogous to Example 1b from 6-methyl-7-[4-(2,3-epoxypropoxy)-phenyl]-1,6-naphthyridin-5(6H)-one and isopropylamine.

Yield: 92% of theory M.p.: 135°–139° C. Elemental analysis: $C_{21}H_{25}N_3O_2$ (367.46) Calculated: C-68.64%; H-6.86%; N-11.44% Found: C-67.03%; H-6.69%; N-11.39%

EXAMPLE 33

6-Methyl-7-[4-2-hydroxy-3-(3,4-dimethoxyphenethyl-amino)-propoxy)-phenyl]-1,6-naphthyridin-5(6H)-one oxalate was prepared analogous to Example 2 from 6-methyl-7-[4-(2,3-epoxypropoxy)-phenyl]-1,6-naphthyridin-5(6H)-one and 2-(3,4-dimethoxy-phenyl)-ethyl-amine.

Yield: 64% of theory M.p.: 82°–95° C. Elemental analysis: $C_{30}H_{33}N_3O_9$ (579.60) Calculated: C-62.17%; H-5.74%; N-7.25% Found: C-61.56%; H-5.80%; N-6.32%

EXAMPLE 34

6-Methyl-7-[4-(2-hydroxy-3-(4-methoxyphenethyl-N-methyl-amino)-propoxy)-phenyl]-1,6-naphthyridin-5(6H)-one oxalate was prepared analogous to Example 2 from 6-methyl-7-[4-(2,3-epoxypropoxy)-phenyl]-1,6-naphthyridin-5(6H)-one and N-[2-(4-methoxyphenyl)-ethyl]-N-methyl-amine.

Yield: 61% of theory M.p.: 66°–73° C. Elemental analysis: $C_{30}H_{33}N_3O_8$ (563.60) Calculated: C-63.93%; H-5.90%; N-7.45% Found: C-63.94%; H-5.75%; N-7.14%

EXAMPLE 35

6-Methyl-7-[4-(2-hydroxy-3(N-3,4,5-trimethoxyphenethyl-N-methyl-amino)-propoxy)-phenyl]-1,6-naphthyridin-5(6H)-one oxalate was prepared analogous to Example 2 from 6-methyl-7-[4-(2,3-epoxypropoxy)-phenyl]-1,6-naphthyridin-5(6H)-one and N-[2-(3,4,5-trimethoxy-phenethyl]-N-methyl-amine.

Yield: 35.5% of theory M.p.: 87°–95° C. Elemental analysis: $C_{32}H_{37}N_3O_{10}$ (623.7) Calculated: C-61.63%; H-5.98%; N-6.74% Found: C-61.38%; H-5.84%; N-6.77%

EXAMPLE 36

6-Methyl-7-[4-(2-hydroxy-3-tert. butylamino-propoxy)-phenyl]-1,6-naphthyridin-5(6H)-one oxalate was prepared analogous to Example 1b from 6-methyl-7-[4-(2,3-epoxypropoxy)-phenyl]-1,6-naphthyridin-5(6H)-one and tert. butylamine.

Yield: 41% of theory M.p.: 248°–250° C. Elemental analysis: $C_{24}H_{29}N_3O_7$ (471.5) Calculated: C-61.14%; H-6.20%; N-8.91% Found: C-60.70%, H-6.42%; N-8.89%

EXAMPLE 37

6-Methyl-7-[4-(2-hydroxy-3-diethylamino-propoxy)-phenyl]-1,6-naphthyridin-5(6H)-one oxalate was prepared analogous to Example 1b from 6-methyl-7-[4-(2,3-epoxypropoxy)-phenyl]-1,6-naphthyridin-5(6H)-one and diethylamine.

Yield: 70% of theory M.p.: 143°–145° C. Elemental analysis: $C_{24}H_{29}N_3O_7$ (471.4) Calculated: C-61.14%; H-6.20%; N-8.91% Found: C-61.22%; H-6.25%; N-9.01%

EXAMPLE 38

6-Methyl-7-[4-(3-(3,4-dimethoxy-phenethyl-N-methyl-amino)-propoxy)-phenyl]-1,6-naphthyridin-5(6H)-one oxalate was prepared analogous to Example 3b from 6-methyl-7-[4-(3-chloropropoxy)-phenyl]-1,6-naphthyridin-5(6H)-one and N-[2-(3,4-dimethoxy-phenyl)-ethyl]-N-methyl-amine.

Yield: 45% of theory M.p.: 167°–170° C. Elemental analysis: $C_{31}H_{35}N_3O_8$ (577.6) Calculated: C-64.46%; H-6.11%; N-7.27% Found: C-64.45%; H-6.16%; N-7.05%

EXAMPLE 39

6-Methyl-7-[4-(3-(4-methoxyphenethyl-N-methyl-amino)-propoxy)-phenyl]-1,6-naphthyridin-5(6H)-one oxalate was prepared analogous to Example 3b from 6-methyl-7-[4-(3-chloropropoxy)-phenyl]-1,6-naphthyridin-5(6H)-one and N-[2-(4-methoxyphenyl)-ethyl]-N-methyl-amine.

Yield: 45% of theory M.p.: 188°–190° C. Elemental analysis: $C_{30}H_{33}N_3O_7$ (547.6) Calculated: C-65.80%; H-6.07%; N-7.67% Found: C-66.72%; H-5.85%; N-7.74%

The compounds of the present invention, that is,

A = 2-Methyl-3-[4-(2-hydroxy-3-tert. butylamino-propoxy)-phenyl]-7-methoxy-isoquinolin-1 (2H)-one, B = 2-Methyl-3-[2-(2-hydroxy-3-isopropylamino-propoxy)-phenyl]-7-methoxy-isoquinolin-1 (2H)-one-oxalate, C = 2-Methyl-3-[2-(2-hydroxy-3-isopropylamino-propoxy)-4-methoxy-phenyl]-7-methoxy-isoquinolin-1 (2H)-one-oxalate, D = 2-Methyl-3-[2-(2-hydroxy-3-tert. butylamino-propoxy)-4-methoxy-phenyl]-7-methyoxy-isoquinoline-1 (2H)-one-oxalate, E = 2-Methyl-3-[4-(2-hydroxy-3-tert. butylamino-propoxy)-phenyl]-6,7-dimethoxy-isoquinolin-1 (2H)-one.

F = 2-Methyl-3-[4-(2-hydroxy-3-isopropylamino-propoxy)-phenyl]-6,7-dimethoxy-isoquinolin-1 (2H)-one, G = 2-Methyl-3-[3-methoxy-4-(2-hydroxy-3-isopropylamino-propoxy)-phenyl]-7-methoxy-isoquinolin-1 (2H)-one, and H = 2-Methyl-3-[4-(2-hydroxy-3-isopropylamino-propoxy)-phenethyl]-7-methoxy-isoquinolin-1 (2H)-one.

(1.) Effect on blood circulation:

The blood circulation tests were performed on dogs with a body weight of 19–30 kg under chloralose-urethane-nembutalanesthesia (54+270+10 mg/kg i.v.). After opening the thorax in the 4th left intercostal space, artificial respiration was applied to the animals with room air by means of an Harvard-Respirator.

The arterial blood-pressure was measured in an arteria carotis with a Statham-transducer; the heart rate was measured electronically from the sequence of R-peaks of the electrocardiogram. The maximum rate of pressure increase (dp/dt max) in the left ventricle was measured by means of a Konigsberg pressure-receiver and a Grass differentiation amplifier.

All parameters were recorded by means of a direct-writer. For inhibition of coagulation the animals were given 10 mgm/kg of potassium polyethylenesulfonate i.v. in 20% of polydiol. The test compounds were intravenously administered to 4–6 dogs per compound.

The following table shows the results obtained:

Table I

| Compound | Dose mgm/kg i.v. | Effect on average arterial blood pressure [mm Hg] | Duration in minutes | Decrease in heart rate [beats/min] | Duration in minutes | Decrease of contractility dp/dt max. % | Duration in minutes |
| --- | --- | --- | --- | --- | --- | --- | --- |
| A | 1.0 | −20 ± 2 | 50 | 29 ± 15 | 36 | 50 ± 10 | 44 |
| B | 1.0 | −24 ± 2 | 41 | 19 ± 6 | 50 | 51 ± 7 | 47 |
| C | 1.0 | −17 ± 3 | 40 | 38 ± 2 | 50 | 53 ± 6 | 50 |
| D | 0.25 | −6 ± 3 | 24 | 15 ± 5 | 27 | 36 ± 13 | 28 |
| E | 1.0 | −18 ± 11 | 11 | 25 ± 6 | 51 | 52 ± 8 | 51 |
| F | 1.0 | −7 ± 3 | 17 | 12 ± 6 | 31 | 33 ± 6 | 43 |
| G | 0.25 | −3 ± 2 | 20 | 37 ± 5 | 54 | 48 ± 6 | 48 |
| H | 1.0 | −25 ± 15 | 20 | 34 ± 10 | 47 | 53 ± 13 | 47 | those embraced by formula I and their non-toxic, pharmacologically acceptable acid addition salts, have useful pharmacodynamic properties. More particularly, they exhibit anti-anginous, anti-arrhythmic and β-adrenergic-receptor blocking activities in warm-blooded animals, such as dogs, and are therefore useful for the treatment of anginose disorders, especially angina pectoris, cardiac arrhythmia and hypertension.

The above-indicated pharmacological properties were ascertained by the test methods described below, and the tables show the results obtained for a few representative species, where (2.) Effect on the force of contraction and frequency of the isolated guinea pig auricle In spontaneously beating isolated auricles of guinea pigs, which were kept in carbogen-aerated (05% $O_2$+5% $CO_2$) Krebs-Henseleit-solution at a temperature of 37° C., and at predetermined concentrations of the test compounds, the maximum developed tension (isometric force of contraction) and the frequency were measured:

Table II

| Compound | Dose gm/ml | Decrease in maximum force of contraction | Decrease in frequency |
|---|---|---|---|
| A | $10^{-5}$ | 50% | 23% |
|   | $3.10^{-5}$ | 82% | 30% |
| C | $3.10^{-6}$ | 17% | 15% |
|   | $10^{-5}$ | 29% | 29% |
| D | $3.10^{-5}$ | 64% | 40% |
| E | $3.10^{-5}$ | 54% | 31% |
|   | $10^{-4}$ | 72% | 46% |
| F | $10^{-5}$ | 30% | 22% |
|   | $3.10^{-5}$ | 43% | 29% |
| G | $10^{-5}$ | 35% | 22% |
|   | $3.10^{-5}$ | 48% | 37% |

(3.) Determination of acute toxicity

The acute toxicity of the test compounds was determined in mice (observation period: 14 days) after oral or intravenous administration. The $LD_{50}$ was calculated from the percentage of the animals that dies during the observation period after administration of varying doses:

Table III

| Compound | $LD_{50}$ |
|---|---|
| A | 62 mg/kg i.v. |
|   | 460 mg/kg p.o. |
| B | 47 mg/kg i.v. |
| C | 50 mg/kg i.v. (0 out of 5 animals died) |
|   | 500 mg/kg p.o. (0 out of 5 animals died) |

For pharmaceutical purposes the compounds of the present invention are administered to warm-blooded animals peorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powers, solutions, suspensions, emulsions, syrups, suppositories and the like. One effective dosage unit of the compounds according to the present invention is from 0.83 to 4.2 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 40

Tablets

The tablet composition is compounded from the following ingredients:

| | |
|---|---|
| 2-Methyl-3-[4-(2-hydroxy-3-tert . butylamino-propoxy)-phenyl]-7-methoxy-isoquinolin-1 (2H)-one | 100.0 parts |
| Lactose | 50.0 parts |
| Polyvinylpyrrolidone | 5.0 parts |
| Carboxymethyl cellulose | 19.0 parts |
| Magnesium stearate | 1.0 parts |
| Total | 175.0 parts |

Preparation:

The active ingredient and the lactose are intimately admixed with each other, the mixture is moistened with an aqueous solution of the polyvinylpyrrolidone and granulated, the granulate is dried and admixwd with the remaining ingredients, and the resulting composition is compressed into 175 mgm-tablets. Each tablet is an oral dosage unit composition containing 100 mgm of the active ingredient.

EXAMPLE 41

Suppositories:

The suppository composition is compounded from the following ingredients:

| | |
|---|---|
| 2-Methyl-3-[4-(2-hydroxy-3-isopropylamino-propoxy)-phenyl]-6,7-dimethoxy-isoquinolin-1(2H)-one | 150.0 parts |
| Suppository base (e.g. cocoa butter) | 1550.0 parts |
| Total | 1700.0 parts |

Preparation:

The active ingredient is homogeneously stirred into the molten suppository base, and 1700 mgm-portions of the mixture are poured into cooled suppository molds and allowed to harden therein. Each suppository is a rectal dosage unit composition containing 150 mgm of the active ingredient.

EXAMPLE 42

Coated pills

The pill core composition is compounded from the following ingredients:

| | |
|---|---|
| 2-Methyl-3-[4-(2-hydroxy-3-tert . butylamino-propoxy)-phenyl]-7-methoxy-isoquinolin-1 (2H)-one | 50.0 parts |
| Corn starch, dry | 20.0 parts |
| Soluble starch | 2.0 parts |
| Carboxymethyl cellulose | 7.0 parts |
| Magnesium stearate | 1.0 parts |
| | 80.0 parts |

Preparation:

The ingredients are compounded in the same manner as in Example 40, and the composition is compressed into 80 mgm-pill cores which are subsequently coated with a thin shell consisting essentially of sugar and gum arabic. Each coated pill is an oral dosage unit composition containing 50 mgm of the active ingredient.

EXAMPLE 43

Suspension

The suspension is compounded from the following ingredients:

| | |
|---|---|
| 2-Methyl-3-[4-(2-hydroxy-3-isopropylamino-propoxy)-phenyl]-6,7-dimethoxy-isoquinolin-1 (2H)-one | 5.0 parts |
| Carboxymethyl cellulose | 0.1 parts |
| Methyl p-hydroxy-benzoate | 0.05 parts |
| Propyl p-hydroxy-benzoate | 0.01 parts |
| Sugar | 10.0 parts |
| Glycerin | 5.0 parts |
| 70% sorbitol solution | 20.0 parts |
| Flavoring | 0.3 parts |
| Distilled water q.s. ad | 100.0 parts |

Preparation:

The p-hydroxy-benzoates, the glycerin and the carboxymethyl cellulose are dissolved in the distilled water at 70° C. while stirring. The resulting solution is cooled to room temperature, and the active ingredient is homogeneously dispersed therein. Thereafter, the sugar, the sorbitol solution and the flavoring are added and dissolved in the suspension, and the resulting composition is de-aerated in vacuo, while stirring. 5 ml of the suspension are an oral dosage unit composition containing 250 mgm of the active ingredient.

Any one of the other compounds embraced by formula I or a non-toxic, pharmacologically acceptable acid addition salt thereof may be substituted for the particular active ingredient in Examples 40 through 43. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

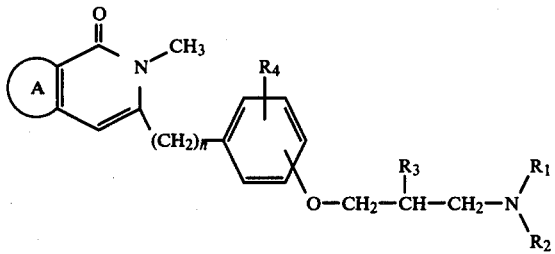

wherein
A is benzo, methoxybenzo, dimethoxybenzo or 1-pyrido;
$R_1$ is hydrogen or alkyl of 1 to 3 carbon atoms;
$R_2$ is alkyl of 1 to 4 carbon atoms or X—$R_6$,
  where X is straight alkylene of 2 or 3 carbon atoms or hydroxy-substituted straight alkylene of 2 or 3 carbon atoms, and
  $R_6$ is amino, carbalkoxy of 2 to 6 carbon atoms, phenyl, methoxyphenyl, dimethoxyphenyl, trimethoxyphenyl, methylphenyl, phenoxy, methoxyphenoxy or methylphenoxy;
$R_3$ is hydrogen or hydroxyl;
$R_4$ is hydrogen or methoxy; and
n is 0, 1 or 2;
or a non-toxic, pharmacologically acceptable acid salt thereof.

2. A compound of claim 1, where
A is benzo, methoxybenzo, dimethoxybenzo or 1-pyrido;
$R_1$ is hydrogen, methyl, ethyl, n-propyl or isopropyl;
$R_2$ is methyl, ethyl, n-propyl, n-butyl, n-pentyl, n-hexyl, isopropyl, isobutyl, isoamyl, tert. butyl, tert. pentyl or —X—$R_6$,
  where X is methylene, ethylene, hydroxyethylene, propylene, hydroxypropylene or butylene, and
  $R_6$ is phenyl, methoxyphenyl, dimethoxyphenyl, trimethoxyphenyl, tolyl, amino, carbomethoxy, carbethoxy, carbopropoxy, carbobutoxy, carbopentoxy, carbisopropoxy, carbo-tert. butoxy, carbo-tert. pentoxy, phenoxy, methylphenoxy or methoxyphenoxy;
$R_4$ is hydrogen, methoxy, ethoxy, propoxy or isopropoxy;
$R_5$ is methyl, ethyl, n-propyl or isopropyl; and
n is 0, 1 or 2;
or a non-toxic, pharmacologically acceptable acid addition salt thereof.

3. A compound of claim 1, where
A is benzo, methoxybenzo, dimethoxybenzo or 1-pyrido;
$R_1$ is hydrogen, methyl or ethyl;
$R_2$ is ethyl, isopropyl, tert. butyl or —X—$R_6$;
X is straight alkylene of 2 to 3 carbon atoms or hydroxy-substituted straight alkylene of 2 to 3 carbon atoms;
$R_6$ is phenyl; methoxyphenyl, dimethoxyphenyl; trimethoxyphenyl; amino; tolyl; isopropoxycarbonyl; tert. butoxycarbonyl; phenoxy; methylphenoxy; or methoxyphenoxy;
$R_3$ is hydrogen or hydroxyl;
$R_4$ is hydrogen or methoxy; and
n is 0, 1 or 2;
or a non-toxic, pharmacologically acceptable acid addition salt thereof.

4. A compound of claim 1, where
A is benzo, 2-methoxy-benzo or 2,3-dimethoxybenzo;
$R_1$ is hydrogen;
$R_2$ is isopropyl or tert. butyl;
$R_3$ is hydroxyl;
$R_4$ is hydrogen or methoxy; and
n is 0, 1 or 2;
or a non-toxic, pharmacologically acceptable acid addition salt thereof.

5. A compound of claim 1, which is 2-methyl-3-[4-(2-hydroxy-3-tert. butylamino-propoxy)-phenyl]-7-methoxy-isoquinolin-1 (2H)-one or a non-toxic pharmacologically acceptable acid addition salt thereof.

6. A compound of claim 1, which is 2-methyl-3-[2-(2-hydroxy-3-isopropylamino-propoxy)-phenyl]-7-methoxy-isoquinolin-1 (2H)-one or a non-toxic, pharmacologically acceptable acid addition salt thereof.

7. A compound of claim 1, which is 2-methyl-3-[2-(2-hydroxy-3-isopropylamino-propoxy)-4-methoxyphenyl]-7-methoxy-isoquinolin-1 (2H)-one or a non-toxic, pharmacologically acceptable acid addition salt thereof.

8. A hypotensive pharmaceutical dosage unit composition consisting essentially of an inert pharmaceutical carrier and an effective hypotensive amount of a compound of claim 1.

9. The method of lowering the blood pressure of a warm-blooded animal in need thereof, which comprises perorally, parenterally or rectally administering to said aminal an effective hypotensive amount of a compound of claim 1.

* * * * *

UNITED STATES PATENT AND TRADEMARK OFFICE
CERTIFICATE OF CORRECTION

PATENT NO. : 4,154,837
DATED : May 15, 1979
INVENTOR(S) : Joachim Heider, Volkhard Austel, Wolfgang Eberlein, Rudolf Kadatz, and Jürgen Dammgen It is certified that error appears in the above-identified patent and that said Letters Patent are hereby corrected as shown below:

Col. 2, line 64 - to the right of the formula insert

--(III)--

Col. 9, line 26 - "and N-b" should read --and N- --

Col. 11, line 20 - "methoxy-isoquinolino-" should read

--methoxy-isoquinolin--.

Signed and Sealed this

Twenty-third Day of October 1979

[SEAL]

Attest:

RUTH C. MASON
Attesting Officer

LUTRELLE F. PARKER
Acting Commissioner of Patents and Trademarks